(12) United States Patent
Hon (10) Patent No.: US 10,238,149 B2
(45) Date of Patent: Mar. 26, 2019

(54) ELECTRONIC SMOKING DEVICE WITH AEROSOL MEASUREMENT

(71) Applicant: FONTEM HOLDINGS 1 B.V., Amsterdam (NL)

(72) Inventor: Lik Hon, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 0 days.

(21) Appl. No.: 15/538,595

(22) PCT Filed: Dec. 25, 2014

(86) PCT No.: PCT/CN2014/094909
§ 371 (c)(1),
(2) Date: Jun. 21, 2017

(87) PCT Pub. No.: WO2016/101203
PCT Pub. Date: Jun. 30, 2016

(65) Prior Publication Data
US 2017/0347710 A1   Dec. 7, 2017

(51) Int. Cl.
*A24F 47/00*   (2006.01)
*A61M 15/06*   (2006.01)
(Continued)

(52) U.S. Cl.
CPC ......... *A24F 47/008* (2013.01); *A61M 11/042* (2014.02); *A61M 15/06* (2013.01); *G01N 9/00* (2013.01); *G01N 21/53* (2013.01); *A61M 2016/0021* (2013.01); *A61M 2016/0024* (2013.01); *A61M 2016/0027* (2013.01);
(Continued)

(58) Field of Classification Search
CPC .................................................... A24F 47/008
See application file for complete search history.

(56) References Cited

U.S. PATENT DOCUMENTS

2010/0031967 A1   2/2010   Inagaki
2011/0079220 A1   4/2011   Altobelli et al.
(Continued)

FOREIGN PATENT DOCUMENTS

CN   1190335 A   8/1998
CN   203692550 U   7/2014
(Continued)

OTHER PUBLICATIONS

Patent Cooperation Treaty, International Search Report and Written Opinion, Application No. PCT/CN2014/094909, dated Oct. 10, 2015.
(Continued)

*Primary Examiner* — James Harvey
(74) *Attorney, Agent, or Firm* — Perkins Coie LLP; Kenneth H. Ohriner (57) ABSTRACT

An electronic smoking device and a method for sensing an aerosol during a puff action to the electronic smoking device, the electronic smoking device has an aerosol sensing unit (100) containing a light intensity detector (11, 12) to detect light reflected by an aerosol moving though the aerosol sensing unit (100). A flow speed of the aerosol is derived based on the light intensity detected and a pressure condition within the aerosol sensing unit (100) detected by a pressure sensor.

18 Claims, 6 Drawing Sheets

(51) Int. Cl.
   *A61M 11/04* (2006.01)
   *G01N 9/00* (2006.01)
   *G01N 21/53* (2006.01)
   *A61M 16/00* (2006.01)

(52) U.S. Cl.
   CPC .............. *A61M 2205/3306* (2013.01); *A61M 2205/3334* (2013.01); *A61M 2205/3389* (2013.01); *A61M 2205/3653* (2013.01); *A61M 2205/8206* (2013.01); *G01N 2201/062* (2013.01)

(56) References Cited

U.S. PATENT DOCUMENTS

| | | | |
|---|---|---|---|
| 2014/0300480 A1 | 10/2014 | Xiang | |
| 2014/0338685 A1 | 11/2014 | Amir | |
| 2017/0340009 A1* | 11/2017 | Hon | A24F 47/008 |
| 2017/0347710 A1* | 12/2017 | Hon | G01N 9/00 |

FOREIGN PATENT DOCUMENTS

| | | |
|---|---|---|
| CN | 104146354 A | 11/2014 |
| CN | 203952419 U | 11/2014 |
| CN | 203952437 U | 11/2014 |
| EP | 2156756 A1 | 2/2010 |
| EP | 2404515 A1 | 1/2012 |
| WO | 2004047570 A2 | 6/2004 |
| WO | 2013061248 A1 | 5/2013 |

OTHER PUBLICATIONS

United Kingdom Intellectual Property Office, Combined Search and Examination Report, Application No. GB 1502499.5, dated Apr. 15, 2015.

European Patent Office, extended European Search Report for European Application No. 14908771.0; dated Jul. 25, 2018; 9 pages.

* cited by examiner

ELECTRONIC SMOKING DEVICE WITH AEROSOL MEASUREMENT

RELATED APPLICATION

This Application is a U.S. National Phase Application of International Patent Application No. PCT/CN2014/094909, filed Dec. 25, 2014.

TECHNICAL FIELD

The field of the invention is electronic smoking devices, and more particularly to electronic smoking devices having an aerosol sensing unit.

BACKGROUND OF THE INVENTION

A electronic smoking device, such as an electronic cigarette (e-cig or e-cigarette), electronic cigar, personal vaporizer (PV) or electronic nicotine delivery system (ENDS) is a battery-powered vaporizer which creates an aerosol or vapor. In general, these devices have a heating element that atomizes a liquid solution known as e-liquid.

E-liquid refers to a liquid solution that when heated by an atomizer produces aerosol. The main ingredients of e-liquids are usually a mix of propylene glycol (PG), glycerin (G), and/or polyethylene glycol 400 (PEG400), sometimes with differing levels of alcohol mixed with concentrated or extracted flavorings. Optionally, nicotine may be included. E-liquid is often sold in bottles or pre-filled disposable cartridges. Pre-made e-liquids are manufactured with various tobacco, fruit, and other flavors, as well as with different concentrations of nicotine.

Figure 6:
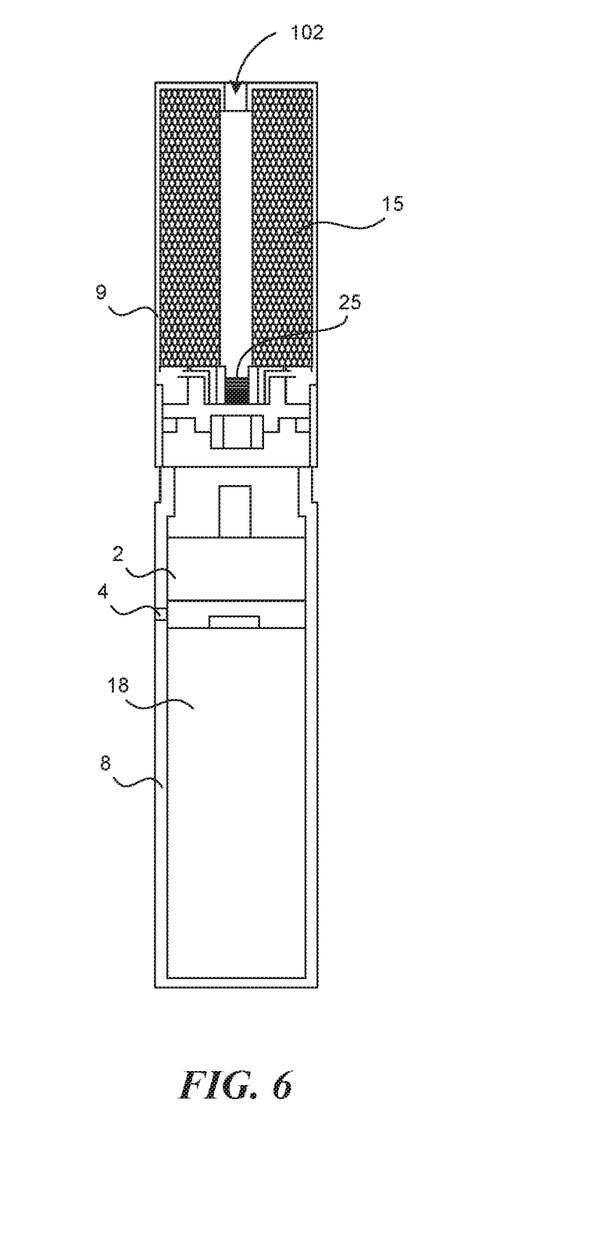
FIG. 6 is a schematic illustration of an electronic cigarette having an aerosol sensing unit and an electronic unit including a processor and memory.

As shown in FIG. 6, in some electronic smoking devices, E-liquid is heated at an atomizer to produce aerosol when the device senses a puff action of a user. The aerosol typically is entrained in air flow through a passageway 12 in the device to a mouthpiece or outlet. The passageway may be aligned on a longitudinal center of the electronic smoking device or along the perimeter of the electronic smoking device.

It is desirable to monitor the amount of the aerosol generated in real-time for the purposes of for example, controlling the amount of aerosol generated during each puff, and estimating the remaining amount of the E-liquid in the E-liquid cartridge or E-liquid container

DETAILED DESCRIPTION

A aerosol sensing unit provides measurements of the amount of aerosol generated during each puff action. This enables an accurate estimation of the amount of e-liquid consumed during each puff which can consequently be used for estimating the remaining e-liquid in the liquid providing unit, such as a liquid cartridge or a liquid bottle. The aerosol measurement may also be used to control the power source so that the electronic smoking device can be shut down when the liquid is consumed completely. The aerosol sensing unit may also eliminate the need for a liquid level detection device in electronic smoking devices.

The aerosol sensing unit may include a light intensity detecting unit including a light emitting element such as light emitting diodes (LED), and a light detecting element such as photodiodes or photomultipliers (PMT) to measure an intensity of the light reflected by the aerosol during a puff. A density of the aerosol can be derived from the measured intensity of the reflected light. A volume of the e-liquid consumed during the puff can then be calculated from the derived density of the aerosol.

The aerosol sensing unit can be an integral part of an atomizer. In this case, a heating element is disposed within a body of the aerosol sensing unit for vaporizing e-liquid conveyed by a wicking material. The vaporized liquid is then mixed with fresh air entered from an inlet provided upstream the heating element to form the aerosol. The aerosol sensing unit can also be a separate component of the electronic smoking device, that is separate from the atomizer.

A pressure sensor can be provided inside the aerosol sensing unit to provide a real time pressure value for deriving a density and/or flow speed of the aerosol. The pressure sensor can also detect a start and/or an end of a puff action by sensing a pressure drop and a pressure rise within the aerosol sensing unit.

The light intensity detecting unit can be arranged in various configurations in response to different measurement methodologies and difference purposes, for example, to facilitate fabrication of the aerosol sensing unit, to increase resolution of the measurement results, and to reduce cost.

Figure 1A:
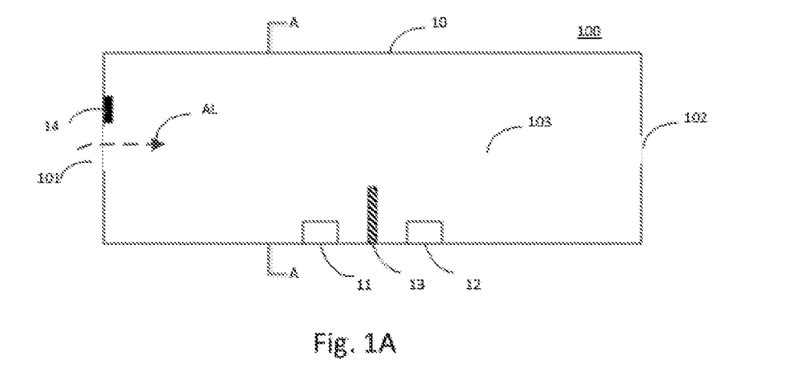
FIG. 1A is a schematic illustration of an aerosol sensing unit for an electronic smoking device.
Figure 1B:
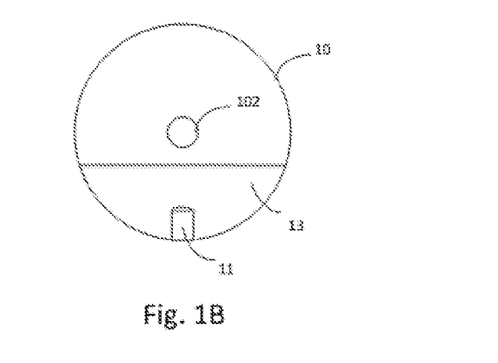
FIG. 1B is a cross section view of FIG. 1 along A-A plane.
Figure 1C:
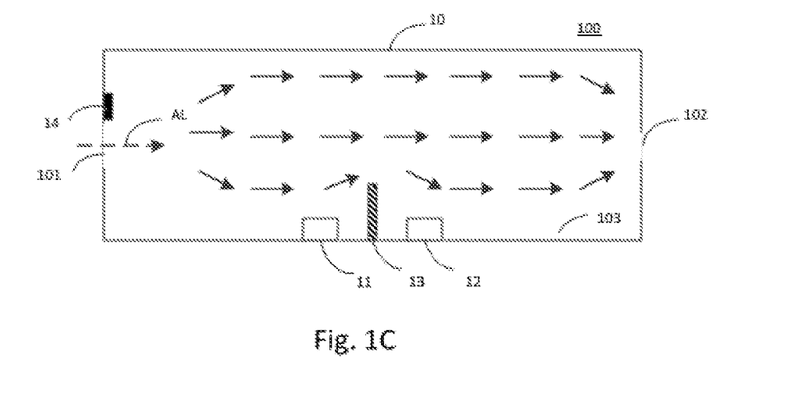
FIG. 1C is a schematic illustration showing an aerosol flow in a chamber of the aerosol sensing unit.

FIGS. 1A and 1B illustrate an aerosol sensing unit 100 according to one embodiment. The sensing unit 100 has a tubular body 10 with an inlet 101 at one end of the body 101 and an outlet 102 at the other end of the body. A chamber 103 is formed within the body between the inlet and the outlet for the aerosol to be measured to pass through. Within the chamber 103, a light emitting element 11, for example, a LED or a laser LED, and a light detecting element 12, for example a photodiode are attached on the side wall of the chamber. In this case, an aerosol AL enters the chamber 103 from the inlet 101, disperses within the chamber and travels along the length of the chamber to the outlet 102 so that the aerosol substantially occupies the entire volume of the chamber as shown in FIG. 1C. The velocity of the aerosol from the inlet to the outlet during each puff may be set at a constant for purposes of calculating aerosol flow.

The cross section of the tubular body 10 can be for example, round, oval, triangular, and rectangular. The shape of the body 10 can be selected to fit within an electronic cigarette device housing 8, 9 shown in FIG. 6. The housing, whether a one-piece housing, or a two piece housing as shown in FIG. 6, generally has dimensions similar to a real tobacco cigarette, typically about 100 mm long with a 7.5 mm diameter, although lengths may range from 70 to 150 or 180 mm, and diameters from 5 to 20 or even 30 mm, especially with refillable tank types of devices.

To reduce background noise when collecting the reflected light, the body 10 can be made from dark color material, for example, plastic, natural rubber or synthetic rubber dyed black, to absorb undesired light reflected or scattered to the cylindrical side wall. The body can alternatively be made from a material having a reflective surface, for example from a stainless steel or aluminum, to reflect back light directed to the side wall. Alternatively, the interior surface of the body 10 can be coated with a light absorbing material or a reflective material to reduce background noise.

The light emitting element 11 and the light detecting element 12 can be arranged close together as illustrated in FIG. 1A. The light emitting element 11 and the light detecting element 12 can also be arranged remotely from or opposite from each other, as illustrated in FIGS. 4D and 4E.

In FIG. 1A, a light barrier 13 is disposed between the light emitting element 20 and the light detecting element 30 to further reduce background noise. The light barrier 13 can designed to prevent the light detecting element 12 from directly detecting light emitted from the light emitting element 11, so that most or all detected light passes though the aerosol.

A sensor such as a pressure sensor 14 may be provided in the body 10 to defect the pressure condition within the chamber 103. The pressure sensor 14 detects a pressure change within the chamber 103, for example a pressure drop or a pressure rise due to a start or an end of a puff action. It can also provide specific pressure value that may be used for deriving the density and/or flow speed of the aerosol. The location of the pressure sensor may affect the result of the measurement. In the configuration illustrated in FIG. 1A, the pressure sensor 14 is placed near the inlet 101 to increase sensitivity to pressure changes. Other types of sensors, such as a flow velocity sensor may optionally be used.

Once a pressure change inside the chamber 103 is detected by the pressure sensor 14, the light emitting element is activated. The light emitting element 11 emits light into or through the aerosol AL. The emitted light is reflected by the aerosol droplets or particles and the reflected light is collected by the light detecting element 12. A corresponding electrical signal is generated by the light detecting element 12, which is then provided to a processor to derive the density of the aerosol AL. The pressure sensor 14 also provides pressure value used for deriving the density of the aerosol C.

The density of the aerosol C can be derived on the basis of Beer-Lambert law according to Equation 1:

$$\frac{I}{I_0} = e^{-\varepsilon l c} \qquad \text{Equation 1}$$

wherein I is the intensity of light received by the light detecting element; $I_0$ is the intensity of light emitted by the light emitting element; ε is an absorptivity of the aerosol; l is the distance the light travels through the aerosol, and c is the density of the aerosol.

The intensity of light emitted by the light emitting element $I_0$ can be measured in advance and stored in a memory unit. Alternatively, the intensity of the light emitted can be measure in-real time by a secondary sensor in the light path, so that the intensity value stored in the memory unit can be updated.

In the aerosol sensing unit illustrated in FIG. 1A, l can be calculated based on the distance between the light emitting element 11 and the light detecting element 12, and the diameter of the tubular body 10.

The absorptivity of the aerosol ε is a function of the ambient temperature and pressure and therefore can be derived in advance and stored with in the memory unit.

Once the density of the aerosol is derived, the flow speed of the aerosol can then be derived on the basis of the Bernoulli's principle according to Equation 2:

$$\frac{1}{2}\rho v^2 + \rho g h + P = \text{constant} \qquad \text{Equation 2}$$

wherein v is the flow speed of the aerosol at a chosen point; ρ is the density of the aerosol; P is the pressure at the chosen point; g is the acceleration due to gravity; and h is the piezometric head or hydraulic head (the sum of the elevation z and the pressure head).

The flow speed of the aerosol can then be used to derive the volume of aerosol generated during the puff according to Equation 3.

$$\text{Vol}=S*v*t \qquad \text{Equation 3}$$

Wherein Vol is the volume of the aerosol passing through the chamber during a puff; S is the cross section area of the chamber; v is the flow speed of the aerosol; and t is the duration of a puff action.

The speed of the aerosol used for deriving the volume of the aerosol generated during a puff may be a mean value which is for example an average flow speed of a plurality of flow speed values derived from several processes repeatedly performed in one puff. The duration of the puff can be determined by measuring the duration of a pressure drop and a pressure rise detected by the pressure sensor or can be an empirical value stored in advance in the memory unit.

The light emitting element and the light detecting element in this aerosol sensing unit can be arranged in various configurations as required. These configurations will be explained with reference to the atomizer described below.

Figure 2A:
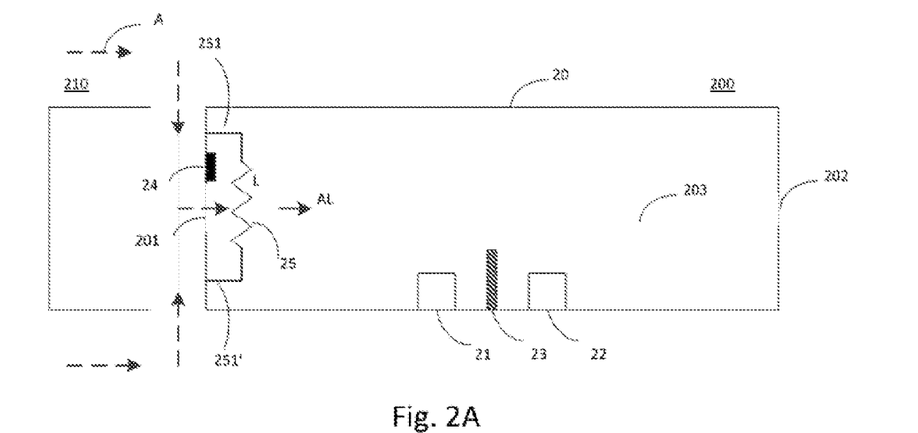
FIG. 2A is a schematic illustration of an atomizer having an aerosol sensing unit and a heating element positioned in alignment with an inlet of the aerosol sensing unit.

FIG. 2A illustrates an atomizer 200 including an aerosol sensing unit. The atomizer includes a tubular body 20 having an inlet 201 at one end of the body 20 and an outlet 202 at the other end of the body. A chamber 203 is formed within the body between the inlet and the outlet for the aerosol to pass through. A light intensity detecting unit is disposed a light emitting element 21 within the chamber 203. The light intensity detecting unit can have for example, a LED or a laser LED is disposed on the side wall of the chamber. A light detecting element 22, for example a photodiode, is also disposed on the side wall of the chamber, downstream the light emitting element. In this case, aerosol AL enters the chamber 203 from the inlet 201 via suction by the user, is dispersed within the chamber and travels along the chamber to the outlet 202, so that the aerosol substantially occupies the entire volume of the chamber.

As shown in FIG. 2A, a heating element 25 is arranged upstream the light detecting element 21 to produce vaporized e-liquid. The vaporized e-liquid mixes with the fresh air sucked in through the inlet to form the aerosol. The heating element 25 may be a heating coil 25 having two leads 251, 251' connected to a power supply. The heating element 25 can be placed anywhere upstream the light detecting element and it is desirable to place the heating element near the inlet 201 so that the aerosol travels approximately the entire length of the tubular body 20. In this arrangement, E-liquid may flow directly from a liquid containing unit along the leads to the heating element 25.

As illustrated in FIG. 2A, the heating element can be placed in alignment with the inlet 201 so that fresh air A flow through the inlet 101 is directed to the heating element and mixed with the vaporized e-liquid L to form the aerosol AL. The aerosol is then dispersed within the chamber and travels along the chamber to the outlet 202.

Figure 2B:
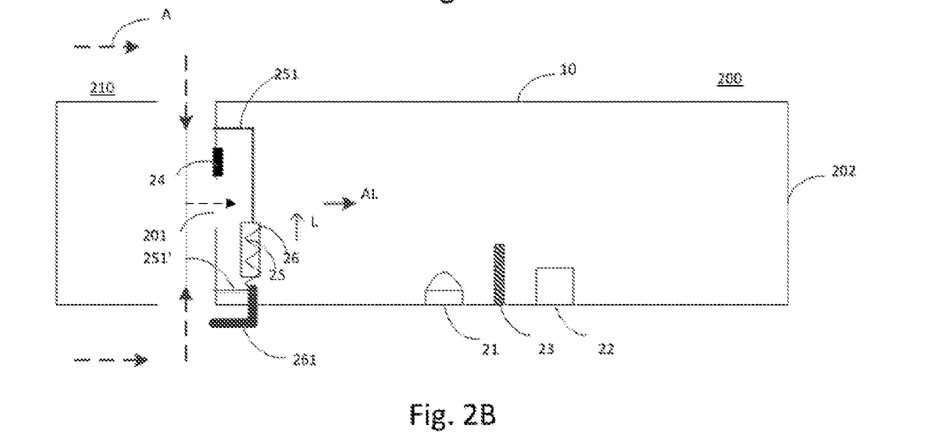
FIG. 2B is a schematic illustration of an atomizer having an aerosol sensing unit and a heating element positioned below the inlet of the aerosol sensing unit.

In FIG. 2B, the heating element 25 can be placed at a level below the inlet 201 so that the vaporized e-liquid L travels in a direction orthogonal to the flow of the fresh air A and mixes with the fresh air above the heating element to form the aerosol AL.

The heating element may also be a coil-less design. For example, the heating element may be formed by a bundle, mat or matrix of fibers, such as carbon fibers, optionally treated with a conductive material or metal.

Figure 2C:
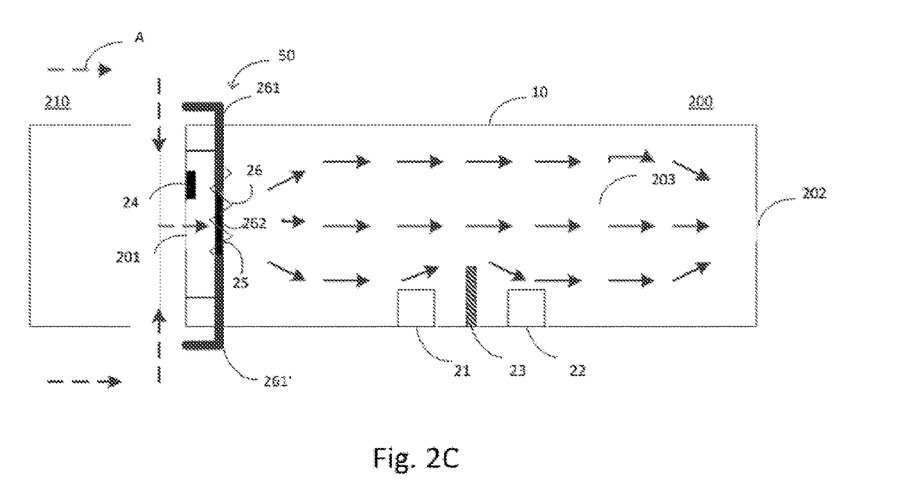
FIG. 2C is a schematic illustration of an atomizer having an aerosol sensing unit, a heating element and a wicking element.

Turning to FIGS. 2B and 2C, a wicking element 26 may be provided for conducting e-liquid to the heating element more efficiently. The wicking element 26 may have a liquid holding portion 262 wound by the heating element 25, and two leads 261, 261' in FIG. 2C, or one lead 261 in FIG. 2B, connected to the liquid containing unit for conveying e-liquid from the liquid supply to the liquid holding portion. Referring momentarily to FIG. 6, the liquid supply 15 may be container or space for holding e-liquid.

In the embodiments illustrated in FIGS. 2A-2C, the processor, the memory unit, power supplying unit and the liquid containing unit can be disposed separately from the atomizer in an electronics unit or board 210.

Figure 3:
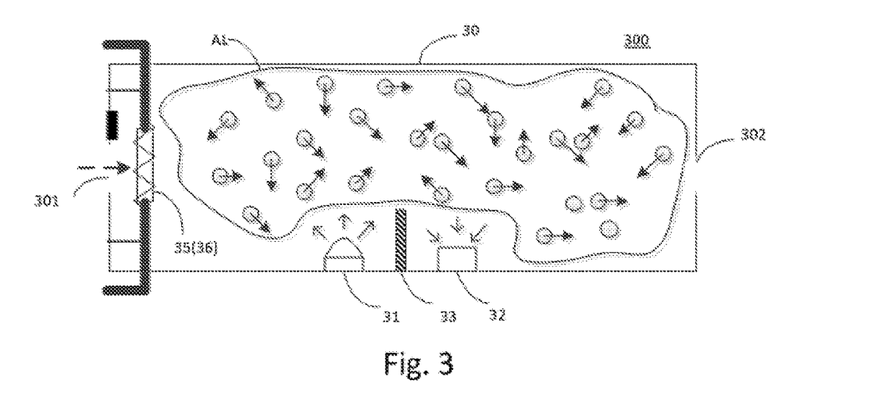
FIG. 3 is a schematic illustration of aerosol diffusion within an atomizer having an aerosol sensing unit.

As shown in FIG. 3, diffuse reflection of the light illustrated with reference to the atomizer 300. The heating element 35 and wicking element 36 are upstream from the light emitting element 31 and the light detecting element 32. Particles or droplets in the aerosol AL reflect the light emitted by the light emitting element 31 in various directions. Some reflected light maybe absorbed by the body 30, and some maybe be directed out of the body from the inlet 301 and the outlet 302. Therefore, the light emitted by the light emitting element 31 is attenuated by the aerosol AL, and the light received at the light detecting element 32 is less intense than the light emitted by the light emitting element 31. The light barrier 33 can act as a light guide so that light travels at least twice the height of the light barrier and will not be received by the light detecting element without passing through the aerosol AL.

Atomizers 400 illustrated in FIGS. 4A-4F can be similar to those described above except that the light emitting element and the light detecting element can be arranged in various configurations to provide optical paths of different lengths. For example the atomizer may have a body 40 having an inlet 401 for taking fresh air A into the body and an outlet 402 for directing an aerosol AL out of the body 40. The atomizer may have a heating element 45 to vaporize e-liquid and a pressure sensor 44 for detecting the pressure condition with the body. A wicking element may also be provided.

Figure 4A:
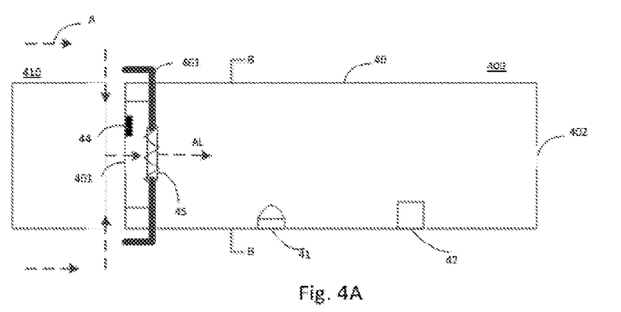
FIG. 4A is a schematic illustration of an atomizer having an aerosol sensing unit with a light emitting element positioned remotely from a light detecting element.
Figure 4B:
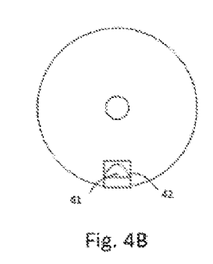
FIG. 4B is a section view taken along line B-B of FIG. 4A.

As shown in FIGS. 4A and 4B, the light emitting element 41 and the light detecting element 42 are attached to a side wall of the body 40 and are arranged in alignment with one another. Both the light emitting element 41 and the light detecting element are placed downstream the heating element 45 and distal to the inlet 41 and the pressure sensor 44. To elongate the optical path, the light detecting element 42 is placed remotely from the light emitting element 41. To achieve a maximum optical path, the light detecting element can be placed proximate the outlet 402 of the body 40.

Figure 4C:
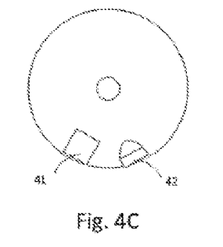
FIG. 4C is a section view taken along line B-B plane and showing another embodiment.
Figure 4D:
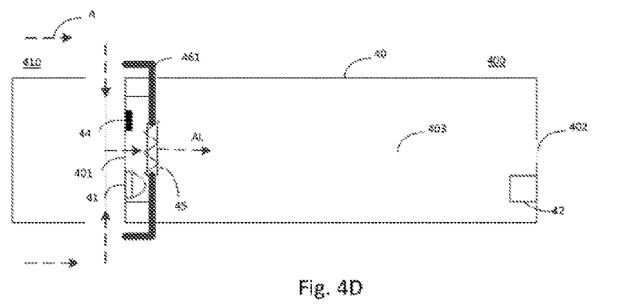
FIG. 4D is a schematic illustration of an atomizer having an aerosol sensing unit with a light emitting element positioned on an end wall of the aerosol sensing unit and opposite to a light detecting element positioned on an opposite end wall of the aerosol sensing unit.
Figure 4E:
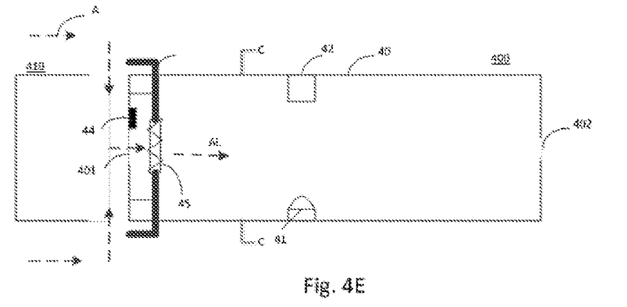
FIG. 4E is a schematic illustration of an atomizer having an aerosol sensing unit with a light emitting element and a light detecting element both positioned on a side wall of the aerosol sensing unit and opposite to each other.

The light emitting element 41 and the light detecting element 42 can also be circumferentially separated by an angle as illustrated in FIG. 4C. The angle can be for example 30, 60 or 90 degrees.

In the configuration illustrated in FIG. 4D, the light emitting element 41 and the light detecting element 42 are arranged opposite to one another with the light emitting element 41 attached to an end wall of the body having the inlet 401 and the light detecting element 42 attached to an opposite end wall of the body 40 having the outlet 402. The light emitting element 41 is placed upstream the heating element 45 and the optical path that the emitted lights travels is the entire length of the chamber 403.

Figure 4F:
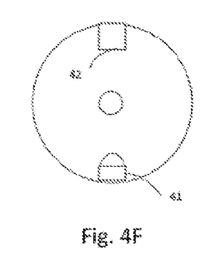
FIG. 4F is a section view taken along line C-C of FIG. 4E.

FIGS. 4E and 4F illustrate another arrangement of the light emitting element and the light detecting element, where the light emitting element 41 is attached to a side wall of the tubular body 40 and the light detecting element 42 is arranged opposite to the light emitting element 41.

Figure 5A:
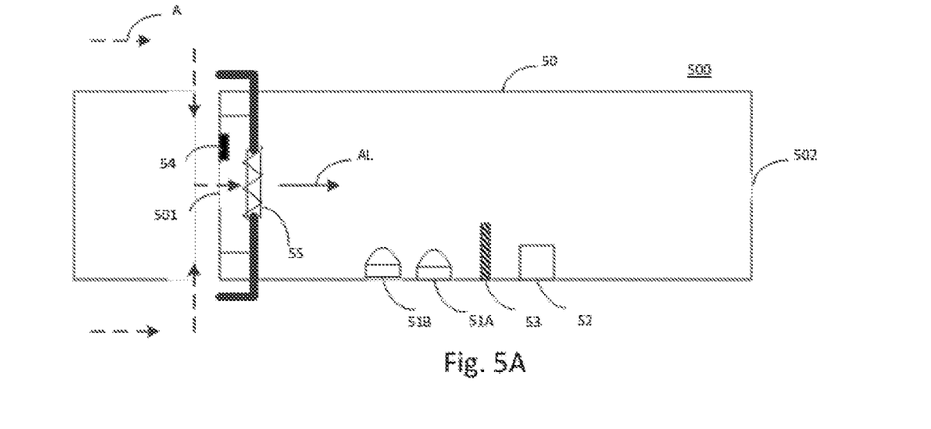
FIG. 5 is a schematic illustration of an atomizer having an aerosol sensing unit with two light emitting elements and a light detecting element.

An atomizer 500 illustrated in FIG. 5 can be similar to the above mentioned embodiment except that the light intensity detecting unit may contain two light emitting elements that emitting lights at different wavelengths. For example the atomizer may have a body 50 having an inlet 501 for taking fresh air A into the body and an outlet 502 for directing an aerosol AL generated out of the body 50. The atomizer may have a heating element 55 to vaporize e-liquid and a pressure sensor 54 for detecting the pressure condition with the body. A wicking element may also be provided if necessary.

In this design, one light emitting element can be a green light LED diode 51A and the other can be a blue light LED diode 51B. Both the blue light and the green light reflected by the aerosol AL are collected by a light detecting element 52 separated from the light emitting elements by a light barrier 53. The intensity of both reflected green and blue lights can be derived separately and the flow speed of the aerosol can be derived using the intensities of both the blue and the green lights.

A aerosol sensing process for an electronic smoking device may comprise following steps:

1) detecting a start of a puff action by detecting a pressure change at the pressure sensor within the body or any other pressure sensor within the electronic smoking device;

2) turning on a heating circuit to provide electric current to the heating element to generate aerosol;

3) activating the light emitting element to emit light to the aerosol;

4) activating the light detecting element to detecting light reflected by the aerosol;

5) deriving the density of the aerosol and then deriving the flow speed of the aerosol accordingly;

6) detecting an end of a puff action and deriving the duration of the puff action;

7) deriving the volume of the aerosol that travels from the inlet to the outlet during the puff action and then deriving the amount of liquid consumed for generating the aerosol.

Parameters for deriving the density of the aerosol and the flow speed of the aerosol, such as the intensity of light emitted by the light emitting element $I_0$, the absorptivity of the aerosol ε, the pressure at the chosen point P; the acceleration due to gravity g; and the piezometric head or hydraulic head h can be stored as empirical values in advance in a memory in the electronics unit. The pressure at a chosen point in the chamber can also be detected in real-time.

The process may further comprise following steps:

Detecting a pressure within the chamber for deriving the flow speed of the aerosol; and Detecting an intensity of the light emitted by the light emitting device $1_0$.

The atomizers described above with reference to the figures can be incorporated into various electronic smoking devices. A processor maybe necessary to perform the steps of the process and a memory unit maybe necessary to store the parameters either detected in real-time or predetermined as empirical values.

The light emitting element and the light detecting element can be collectively called light intensity detecting unit. The heating element can be part of a heating circuit powered by a power supply.

FIG. 6 shows an example of an electronic cigarette which may have a size and shape generally comparable to a real tobacco cigarette. A power source or battery 18 is contained within the electronic cigarette housing, which is optionally divided into a first housing 8 and a second housing 9. One or more inlets 4 are provided in the housing, and an outlet 102 is located at the back end of the electronic cigarette. An electronic controller 2, which may include a processor and memory, is electrically connected to the battery and to the heating element 25, and to the light emitter and detector as described above. A liquid holding container or space 15 may surround a passageway 12 extending from the heating element 25 to the outlet 102.

The examples and embodiments described herein are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Elements and features described in one embodiment may of course be included in other embodiments as well.

The invention claimed is:

1. An electronic smoking device, comprising:
   an atomizer comprising:
      a heating element for generating an aerosol; and
      an aerosol sensing unit comprising—
         a body having an inlet, an outlet and a chamber connecting the inlet and the outlet;
         a light intensity detecting unit for measuring light intensity within the chamber when the aerosol travels through the chamber; and
      a pressure sensor for detecting the pressure within the chamber.

2. The electronic smoking device of claim 1 with a controller including a memory for storing at least one parameter for deriving the flow speed of the aerosol through the chamber.

3. The electronic smoking device of claim 1 wherein the light intensity measurement unit comprises
   a light emitting element for providing lights to the aerosol in the chamber; and
   a light detecting element for collecting lights reflected by the aerosol.

4. The electronic smoking device of claim 3 wherein the light emitting element and the light detecting element are separated by a light barrier.

5. The electronic smoking device of claim 3 wherein the light emitting element and the light detecting element are disposed opposite to one another.

6. The electronic smoking device of claim 5 wherein the light emitting element is arranged upstream from the heating element and the light detecting element is arranged downstream from the heating element.

7. The electronic smoking device of claim 3 wherein the light emitting element is provided on an end wall of the body and the light detecting element is provided on an opposite end wall of the body.

8. The electronic smoking device of claim 3 wherein the light emitting element is disposed remotely from the light detecting element.

9. The electronic smoking device of claim 1 wherein the heating element is provided inside the body.

10. The electronic smoking device of claim 1 wherein the heating element is provided proximate the inlet.

11. The electronic smoking device of claim 1 further comprising a wicking element for conveying e-liquid to the heating element.

12. A method for sensing an aerosol during a puff action to an electronic smoking device, comprising
    generating an aerosol;
    detecting a light intensity of the aerosol;
    deriving the flow speed of the aerosol based on the detected light intensity and pressure of the aerosol;
    determining a duration of the puff action; and
    deriving the volume of the aerosol during the puff action based on the flow speed of the aerosol and the duration of the puff action.

13. The method of claim 12 wherein a heating circuit is turned on when a pressure drop within a body of an atomizer is detected.

14. The method of claim 13 wherein the duration of the puff action is determined by counting the time between a pressure drop and a pressure rise within the body.

15. The electronic smoking device of claim 1 further comprising a controller connected to the light intensity measurement unit and the pressure sensor, the controller deriving a flow speed of the aerosol through the chamber based on the light intensity and pressure within the chamber.

16. An electronic smoking vapor device, comprising:
    a housing;
    a heating element and an aerosol sensing unit both electrically connected to a controller in the housing;
    a liquid supply in the housing positioned to supply liquid to the heating element;

with the aerosol sensing unit including a chamber having an inlet and an outlet, a light intensity detecting unit for measuring light intensity in the chamber, and a pressure sensor for detecting pressure in the chamber;

the controller deriving a mass flow rate of vapor flowing through the chamber based on a light intensity output signal from the light intensity detecting unit and a pressure output signal from the pressure sensor.

17. The device of claim 16 wherein the pressure sensor is within the chamber.

18. The device of claim 16 with the controller deriving a mass flow rate of vapor flowing through the chamber by determining a density of the vapor and a speed of the vapor flowing through the chamber.

* * * * *